(12) United States Patent
Lechmann et al.

(10) Patent No.: US 8,679,181 B2
(45) Date of Patent: Mar. 25, 2014

(54) TOTAL DISC REPLACEMENT DEVICE

(75) Inventors: Beat Lechmann, Grenchen (CH); Roger Buerki, Chur (CH)

(73) Assignee: DePuy Synthes Products, LLC, Raynham, MA (US)

( * ) Notice: Subject to any disclaimer, the term of this patent is extended or adjusted under 35 U.S.C. 154(b) by 372 days.

(21) Appl. No.: 12/438,088

(22) PCT Filed: Aug. 22, 2006

(86) PCT No.: PCT/CH2006/000454
§ 371 (c)(1),
(2), (4) Date: Nov. 19, 2010

(87) PCT Pub. No.: WO2008/022471
PCT Pub. Date: Feb. 28, 2008

(65) Prior Publication Data
US 2011/0054618 A1 Mar. 3, 2011

(51) Int. Cl.
*A61F 2/44* (2006.01)
(52) U.S. Cl.
USPC ............................................. 623/17.14
(58) Field of Classification Search
USPC ............... 623/17.11–17.16; 403/DIG. 7, 149
See application file for complete search history.

(56) References Cited

U.S. PATENT DOCUMENTS

| | | | |
|---|---|---|---|
| 3,820,739 A * | 6/1974 | Graf | 42/573.7 |
| 4,281,941 A * | 8/1981 | Rottenkolber | 403/29 |
| 5,392,693 A * | 2/1995 | Engel et al. | 92/248 |
| 6,315,563 B1 * | 11/2001 | Sager | 433/173 |
| 6,645,248 B2 * | 11/2003 | Casutt | 623/17.12 |
| 7,040,407 B2 * | 5/2006 | Jennings et al. | 166/348 |
| 7,452,380 B2 * | 11/2008 | Zubok et al. | 623/17.14 |
| 7,563,286 B2 * | 7/2009 | Gerber et al. | 623/17.14 |
| 7,704,280 B2 * | 4/2010 | Lechmann et al. | 623/17.15 |
| 7,794,501 B2 * | 9/2010 | Edie et al. | 623/17.12 |
| 8,366,780 B2 * | 2/2013 | Klawitter et al. | 623/18.11 |
| 8,486,146 B2 * | 7/2013 | Ogilvie et al. | 623/17.15 |
| 2002/0068980 A1 * | 6/2002 | Serbousek et al. | 623/22.29 |
| 2003/0074074 A1 * | 4/2003 | Errico et al. | 623/17.14 |
| 2003/0135277 A1 * | 7/2003 | Bryan et al. | 623/17.12 |
| 2003/0187512 A1 * | 10/2003 | Frederick et al. | 623/22.2 |
| 2003/0216810 A1 * | 11/2003 | Ralph et al. | 623/17.14 |
| 2003/0236571 A1 * | 12/2003 | Ralph et al. | 623/17.13 |
| 2004/0133278 A1 * | 7/2004 | Marino et al. | 623/17.14 |
| 2004/0225362 A1 * | 11/2004 | Richelsoph | 623/17.13 |

(Continued)

OTHER PUBLICATIONS

Internation Search Report dated Apr. 18, 2007 for International Application No. PCT/CH2006/000454.

(Continued)

*Primary Examiner* — Ellen C Hammond
*Assistant Examiner* — Jacqueline Johanas
(74) *Attorney, Agent, or Firm* — Baker & Hostetler LLP (57) ABSTRACT

The total disc replacement device (1) comprising a central axis (2), a first and a second apposition plate (3; 5), a first and a second joint component (4; 6) being mutually arranged in a ball joint like manner and being located between said first and second apposition plates (3; 5) and intermediate means (7) being disposed at least between the first apposition plate (3) and the first joint component (4) in such manner that, the first joint component (4) is not freely moveable transversely to the central axis (2) with respect to the first apposition plate (3) under load-free conditions, but a limited movement of the first joint component (4) relative to the first apposition plate (3) transversal to the central axis (2) is allowed under load.

31 Claims, 6 Drawing Sheets

(56) References Cited

U.S. PATENT DOCUMENTS

| | | | |
|---|---|---|---|
| 2004/0267269 A1* | 12/2004 | Middleton et al. | 606/84 |
| 2004/0267369 A1* | 12/2004 | Lyons et al. | 623/17.16 |
| 2005/0001429 A1* | 1/2005 | Abercrombie Simpson | 285/382 |
| 2005/0027363 A1* | 2/2005 | Gordon | 623/17.13 |
| 2005/0033435 A1* | 2/2005 | Belliard et al. | 623/17.14 |
| 2005/0038516 A1 | 2/2005 | Spoonamore | 623/17.14 |
| 2005/0043803 A1 | 2/2005 | Schultz et al. | 623/17.16 |
| 2005/0107881 A1* | 5/2005 | Alleyne et al. | 623/17.15 |
| 2005/0143824 A1* | 6/2005 | Richelsoph et al. | 623/17.16 |
| 2005/0149189 A1 | 7/2005 | Mokhtar et al. | 623/17.11 |
| 2005/0165485 A1 | 7/2005 | Trieu | 623/17.13 |
| 2005/0187632 A1* | 8/2005 | Zubok et al. | 623/17.14 |
| 2005/0251260 A1* | 11/2005 | Gerber et al. | 623/17.13 |
| 2005/0256581 A1* | 11/2005 | Songer et al. | 623/17.16 |
| 2005/0267581 A1* | 12/2005 | Marnay et al. | 623/17.14 |
| 2005/0273169 A1* | 12/2005 | Purcell | 623/17.12 |
| 2006/0015183 A1* | 1/2006 | Gilbert et al. | 623/17.11 |
| 2006/0136063 A1* | 6/2006 | Zeegers | 623/17.14 |
| 2006/0190084 A1* | 8/2006 | Doubler et al. | 623/17.14 |
| 2006/0229724 A1* | 10/2006 | Lechmann et al. | 623/17.11 |
| 2006/0241781 A1* | 10/2006 | Brown et al. | 623/23.43 |
| 2007/0021836 A1* | 1/2007 | Doty | 623/17.13 |
| 2007/0061011 A1* | 3/2007 | de Villiers et al. | 623/17.14 |
| 2007/0073404 A1* | 3/2007 | Rashbaum et al. | 623/17.14 |
| 2007/0162133 A1* | 7/2007 | Doubler et al. | 623/17.11 |
| 2007/0168033 A1* | 7/2007 | Kim et al. | 623/17.13 |
| 2007/0185578 A1* | 8/2007 | O'Neil et al. | 623/17.14 |
| 2007/0203580 A1* | 8/2007 | Yeh | 623/17.13 |
| 2007/0233251 A1* | 10/2007 | Abdou | 623/17.11 |
| 2007/0239283 A1* | 10/2007 | Berger et al. | 623/22.29 |
| 2008/0021557 A1* | 1/2008 | Trieu | 623/17.15 |
| 2008/0065221 A1* | 3/2008 | Alleyne et al. | 623/17.16 |
| 2008/0154383 A1* | 6/2008 | Lechmann et al. | 623/18.11 |
| 2009/0048674 A1* | 2/2009 | Zubok et al. | 623/17.15 |
| 2009/0088853 A1* | 4/2009 | Ogilvie et al. | 623/17.16 |
| 2009/0240336 A1* | 9/2009 | Vander Meulen et al. | 623/18.11 |
| 2009/0270992 A1* | 10/2009 | Gerber et al. | 623/17.16 |
| 2010/0280617 A1* | 11/2010 | Coppes et al. | 623/17.16 |
| 2011/0023810 A1* | 2/2011 | Gerard et al. | 123/193.5 |
| 2011/0087335 A1* | 4/2011 | Newsome et al. | 623/22.29 |
| 2011/0100316 A1* | 5/2011 | Moore et al. | 123/193.5 |
| 2011/0166667 A1* | 7/2011 | Kellar et al. | 623/23.4 |
| 2012/0022664 A1* | 1/2012 | Vander Meulen et al. | 623/23.42 |
| 2012/0053699 A1* | 3/2012 | Meridew | 623/22.29 |
| 2012/0221108 A1* | 8/2012 | Ogilvie et al. | 623/17.16 |

OTHER PUBLICATIONS

International Preliminary Report on Patentability dated Feb. 24, 2009 for International Application No. PCT/CH2006/000454.

* cited by examiner

TOTAL DISC REPLACEMENT DEVICE

The invention relates to a total disc replacement device comprising a first and a second apposition plate, a first and a second joint component and intermediate means disposed between the first apposition plate and the first joint component.

Today implants or prostheses are inserted into the intervertebral space of two adjoining vertebral bodies after removal of a natural intervertebral disc or a nucleus pulposus of an intervertebral disc.

Usually hard material inlays for articulating components of total disc replacement implants are manufactured from super alloys or ceramic materials. These inlays are usually pressed or shrunk into titanium or super alloy bone contact plates, whereby the interface is subject to severe compression stresses.

Total disc replacement devices comprise components for the preservation of segmental motion. Some total disc replacement designs include one or more joints having spherical articulation, e.g., ball-and-socket joint. Materials used to construct the articulating elements can comprise combinations such as metal-on-polymer, metal-on-metal or ceramic-on-ceramic bearing as well as the combination of these materials. Generally, the material combinations aim for minimal wear debris volume and biocompatible wear particles.

An intervertebral implant is known from DE 2003 13 183 AESCULAP, wherein the articulating elements are arranged in an axially rotatable manner in the bone contact plates. The rotation of the articulating elements in the bone contact plates shows the disadvantage of abrasion and a higher clearance.

In embodiments where any rotation should be avoided, inlays are manufactured from hard materials (e.g., metal, metal alloys, and/or ceramic) that have various disadvantages when assembled or otherwise placed into the bone contact plates. Usually the inlay has overlapping dimensions or dimensions that allow the inly to be assembled into the component with a press-fit. However, press-fitting results in high compression forces that can stress the inlay and other components.

A metal inlay may be designed so that it deforms during a press-fit, resulting in a reduction of the clearance of the articulation. High compressive stress to ceramic elements is typically unproblematic if their design is structurally strong. However, total disc replacement devices are relatively small which usually prevents the use of a thick wall design. Since the ceramic material is brittle, and press- or shrink-fitting a ceramic portion of a total disc replacement device can damage the ceramic portion and results in small fragments with sharp edges that could damage. The major blood vessels located near the intervertebral discs. Therefore, stress shielding, particularly to the ceramic material, should be considered in the design.

On this point, the invention intends to provide remedial measures. The invention is based on the objective of providing a total disc replacement device, which allows a clearance-free connection between the apposition plate and the joint component corresponding thereto and which is provided with a stress shielding capacity in order to reduce the compression stress in the concerned interface.

In some embodiments, this invention provides a total disc replacement device that has a central axis and comprises a first and a second apposition plate, a first and a second joint component, and an intermediate means that is disposed at least between the first apposition plate and the first joint component. The first and second joint component can located between the first and second apposition plates. The first and second joint components can be mutually connected or arranged in a ball-joint like manner. The intermediate means can be disposed at least between the first apposition plate and the first joint component in such manner that the first joint component is not freely moveable transversely to the central axis with respect to the first apposition plate under load-free conditions, but a limited movement of the first joint component relative to the first apposition plate transversal to the central axis is allowed under load.

One advantage of the present invention is that it reduces or eliminates compressive stress on the various components of the total disc replacement device. For example, the intermediate means that can be disposed between an apposition plate and a joint component can reduce or eliminate the compressive force needed to assemble the device. Also, the intermediate means can reduce or eliminate the stresses born by the components when implanted into a patient.

Additional advantageous embodiments of the invention are characterized below.

In one embodiment of the invention at least one of the intermediate means is connected to the corresponding apposition plate or to the corresponding joint component with a press-fit. The advantages of such embodiment is to be seen in the facts that stresses due to the high compression forces between the adjacent components are reduced, clearance between the components is avoided and the respective members are firmly kept together. Due to the choice of the soft, elastic or thermoplastic properties of the intermediate means stress can be reduced since the softer component adapts its shape in order to establish a stress-balance.

In a further embodiment the intermediate means are elastically or plastically deformable so that a limited movement of the joint components relative to the corresponding apposition plates is allowed under load.

In another embodiment the press-fit of the intermediate means within the adjacent apposition plate or within the adjacent joint component is obtainable by an elastic deformation of the intermediate means. Due to such embodiments stress shielding is obtainable e.g. with insertion of a polymeric ring.

In a further embodiment the press-fit of the intermediate means within the adjacent apposition plate or within the adjacent joint component is obtainable by a plastic deformation of the intermediate means. Due to such embodiments stress shielding is obtainable e.g. with deformable means being integral with the adjacent apposition plate or the adjacent joint component.

In another embodiment the apposition plates are connected to the corresponding joint component by a plug-socket connection, such that at least a part of the apposition plate and at least a part of the corresponding joint component overlap one another coaxially to the central axis and form an attachment zone, whereby the intermediate means is disposed between the apposition plates and the corresponding joint component only within the attachment zone preferably within the whole attachment zone.

In a further embodiment the intermediate means has a height being smaller than a height of the attachment zone. The advantage of such embodiment can be seen in the fact that due to small height of the intermediate means a major deformation of said intermediate means is allowing.

In another embodiment the Young's modulus of the material of the intermediate means is lower than that of the adjacent apposition plate and/or lower than that of the adjacent joint component. Due to such embodiment the total disc replacement device may comprise components, particularly apposition plates and/or joint components may be made of a material having a high Young's modulus, e.g. use of titan or titan alloys being biocompatible or use of ceramics for the joint components.

In another embodiment the intermediate means consist of the material being selectable of the group of PEEK, PEKK or others members of the PEAK. The advantage of such embodiment can be seen in the fact that thermoplastic semi-crystalline polymers comprise elastic properties with a low grad of creep (alignment of macro-molecules under load). During and after the insertion of the stiff inlay, the intermediate means is able to adapt its shape and distribute the interface stress. Since this process is performed slowly, the risk of rapid load changes is reduced. PEEK, PEKK and other members of the PEAK family, even re-enforced with carbon fibres, PTFE, UHMWPE, all materials must be biocompatible.

In a further embodiment the apposition plates consist of the material being selectable of the group of titanium and its alloys, CoCrMo, or stainless steel and the joint components consist of the material being selectable of the group of ceramics, preferably aluminium oxide, aluminium titanate, silicate ceramics and zirconium oxide, or of the group of CoCrMo or CoCrMoC alloys.

In an additional embodiment the apposition plates and the adjacent joint components consist of the same material. If the design of the apposition plates would be sophisticated ("filigrane"), the use of a material with higher Young's modulus is indicated, i.e. CoCrMo alloy.

In a further embodiment said intermediate means has an essentially cylindrical, preferably circular-cylindrical shape. The advantages of such embodiments can be seen in the facts of uncomplicated manufacturing; homogeneous stress distribution; easier assembly of the snap fit. Furthermore, if the inlay is inserted in-situ (in the intervertebral space), the surgeon is independent from the axial position of the components.

In another embodiment the intermediate means consist of a memory material. After insertion of the intermediate means, they can be heated locally and find its final shape and position.

In a further embodiment said intermediate means and the adjacent apposition plate or the adjacent joint component are connectable by means of a snap-fit, whereby said apposition plates or joint components are provided with lip and said intermediate means are provided with a corresponding undercuts such forming a snap-fit. In another embodiment said apposition plates or joint components are provided with undercuts and said intermediate means are provided with a corresponding lip such forming a snap-fit. The advantage of the additionally form-locking connection of the intermediate means and the corresponding components can be seen in the fact of the prevention of the spontaneous dismantling and easy manufacturing of all components allowed thereby.

In a further embodiment the intermediate means has a spring-shape being corrugated transversely to the central axis. Such corrugated shape allows the use of a metallic material instead of a thermoplastic polymer.

In another embodiment the intermediate means and the corresponding apposition plate or the corresponding join component consist of one piece. The advantage of such embodiments can be seen in the fact of the tension distribution and the reduction of the high loading pressure.

In a further embodiment the intermediate means are designed as plurality of projections, whereby such projections are T-shaped or L-shaped.

The invention and additional configurations of the invention are explained in even more detail with reference to the partially schematic illustration of several embodiments.

Figure 1:
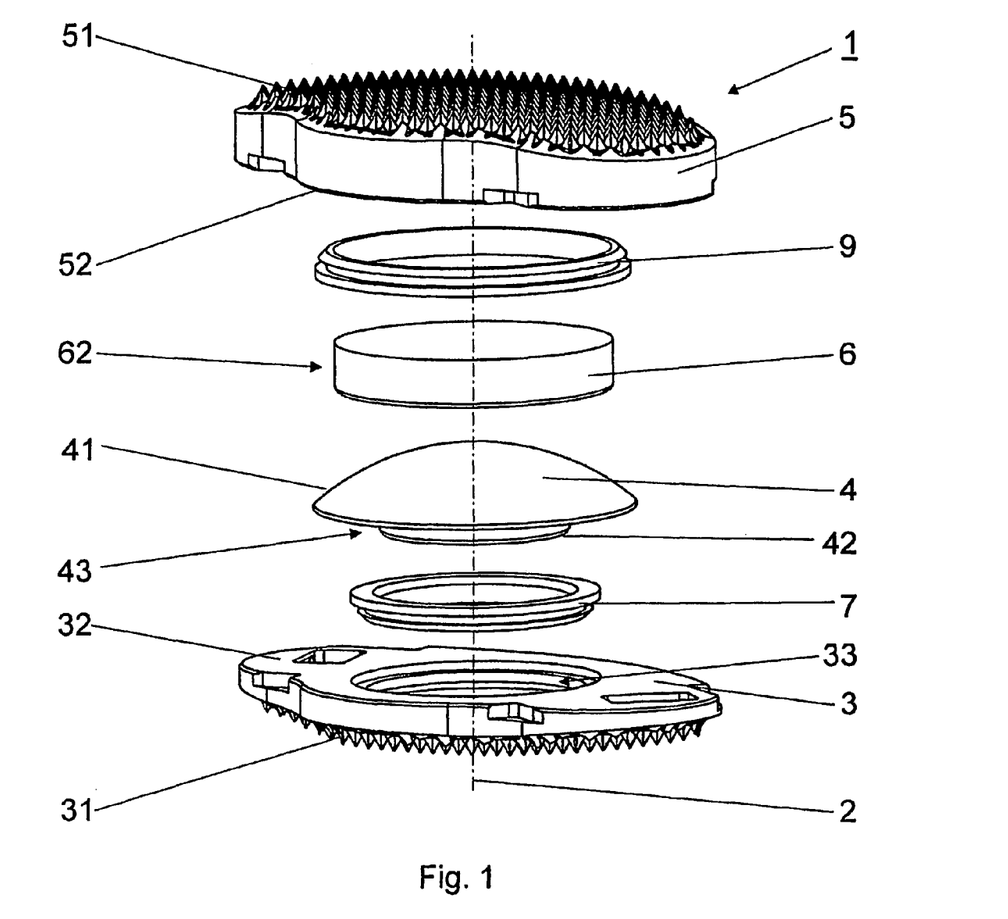
FIG. 1 illustrates an exploded view of an embodiment of the total disc replacement device according to the invention.

The embodiment of the total disc replacement device 1 is shown in FIG. 1. Device 1 comprises a central axis 2, a first and a second apposition plate 3;5, a first and a second joint component 4;6, a first and second intermediate means 7;9.

When device 1 is implanted in a patient, central axis 2 lies essentially parallel to a longitudinal axis of the patient's vertebra. First and second apposition plate 3;5 are disposed transversely to central axis 2. First and second joint components 4;6 are located between said first and second apposition plates 3;5. Together, first and second joint components 4;6 form a ball-joint and are mutually connectable in a ball-joint like manner. First intermediate means 7 is disposed between first apposition plate 3 and first joint component 4. Second intermediate means 9 is disposed between second apposition plate 5 and second joint component 6.

First and second apposition plate 3;5 can be made of titanium or a titanium alloy. First and second joint component 4;6 can be made of a ceramic. The first and second intermediate means 7;9 can be made of an elastic materials, such as, for example a rubber or other type of polymer (e.g., PEEK).

Said first apposition plate 3 comprises a first contact surface 31 and a first intermediate surface 32. Accordingly, said second apposition plate 5 comprises a second contact surface 51 and a second intermediate surface 52. Both contact surfaces 31;51 as well as both intermediate surfaces 32;52 are arranged transversely to said central axis 2. Said first and second apposition plates are arranged relative to each other in a manner that the first and second intermediate surface 32;52 are turned to each other and the first and second contact surfaces 31;51, which is apt to abut the adjacent vertebral bodies, are turned away from each other. Additionally, said first and second apposition plates 3;5 each are provided with a three-dimensional structuring having a form of e.g., spikes and allowing an anchorage of said first and second apposition plates 3;5 in the adjacent vertebral bodies. Said first joint component 4 has a spherical convex sliding surface 41 being arranged concentrically to said central axis 2 and oppositely a first end portion 42 connected to said first apposition plate 3. Said second joint component 6 is provided with a spherical concave sliding surface 61 (FIG. 2) being slideably arranged, on said convex sliding surface 41 and opposite to said concave sliding surface 61 a second end portion 62 connected to said second apposition plate 5. In this manner, the mutual arrangement of concave sliding surface 61 and convex sliding surface 41 provide device 1 with ball-joint like movement.

Figure 2:
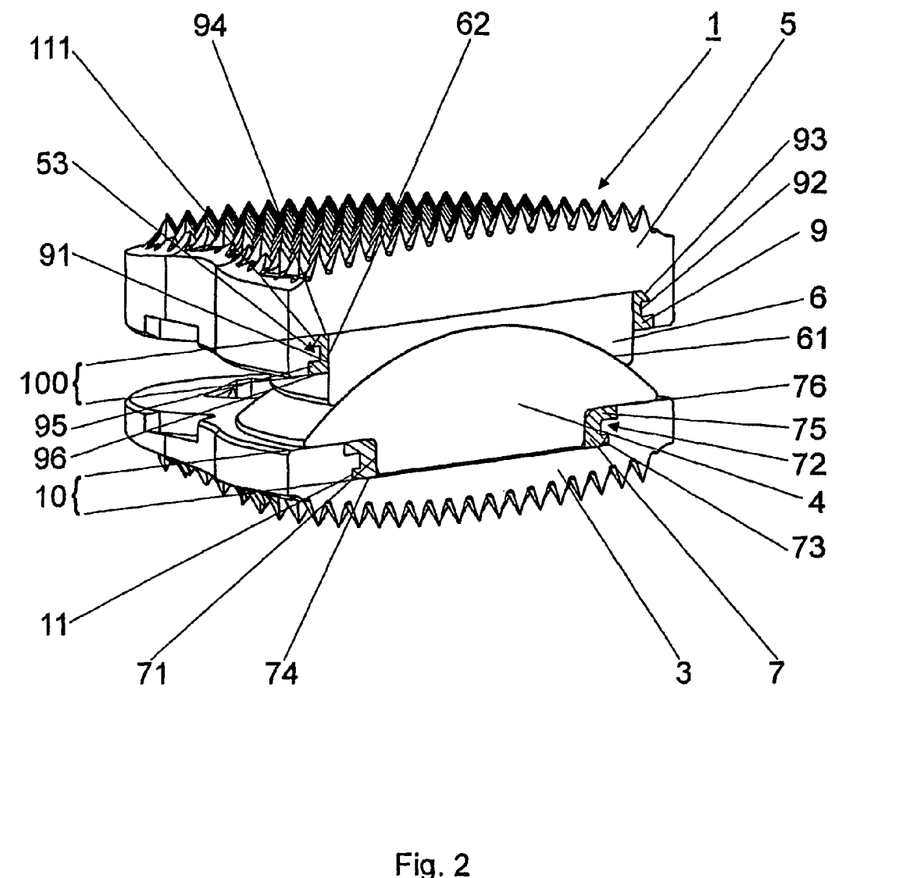
FIG. 2 illustrates a cross-section through the embodiment of FIG. 1.

Said first joint component 4 comprises circular cylindrical projection 43 being coaxial to the central axis 2 and being disposed at said first end portion 42 of said first joint component 4, whereby said first apposition plate 3 comprises the first recess 33 penetrating from said first intermediate surface 32 into said first apposition plate 3. In this manner, said circular cylindrical projection 43 may be inserted into the first recess 33 such said circular cylindrical projection 43 and said first recess 33 forming a first attachment zone 10 (FIG. 2). Furthermore, said second joint component 6 has a circular cylindrical second end portion 62 that may be inserted into the second recess 53 penetrating from said second intermediate surface 52 into said second apposition plate 5 such said second end portion 62 and said second recess 53 forming a second attachment zone 100. In this manner, each of said first and second apposition plates 3;5 is connected to the corresponding joint component 4;6 by a plug-socket connection, whereby the connection between the apposition plates 3;5 and the corresponding joint components (4;6) is clearance-free (i.e. no space between the apposition plates 3;5 and the corresponding joint components (4;6) is left to avoid free motion between them).

Said first intermediate means 7 is configured as a ring radially disposed between said circular cylindrical projection 43 and said first recess 33, whereby said circular cylindrical projection 43 is pressed into the central bore 71 of said first intermediate means 7. At the bottom surface 74 of said first intermediate means 7 the peripheral surface 72 of said first intermediate means 7 comprises a circular lip 73 forming a snap-fit with a circular undercut 11 at the bottom of said first recess 33. Adjacent to said first intermediate surface 32 of said first apposition plate 3 said first recess 33 has a diametrically enlarged section apt to press-fittingly receive a first flange 75 arranged at the top surface 76 of said first intermediate means 7.

Analogously, said second intermediate means 9 is configured as a ring radially disposed between said circular second end portion 62 and said second recess 63, whereby said circular second end portion 62 is pressed into the central bore 91 of said second intermediate means 9. At the top surface 94 of said second intermediate means 9 the peripheral surface 92 of said second intermediate means 9 comprises a circular lip 93 forming a snap-fit with a circular undercut 111 at the bottom of said second recess 53. Adjacent to said second intermediate surface 52 of said second apposition plate 5 said second recess 53 has an diametrically enlarged section apt to press-fittingly receive a second flange 95 arranged at the bottom surface 96 of said second intermediate means 9.

Figure 3:
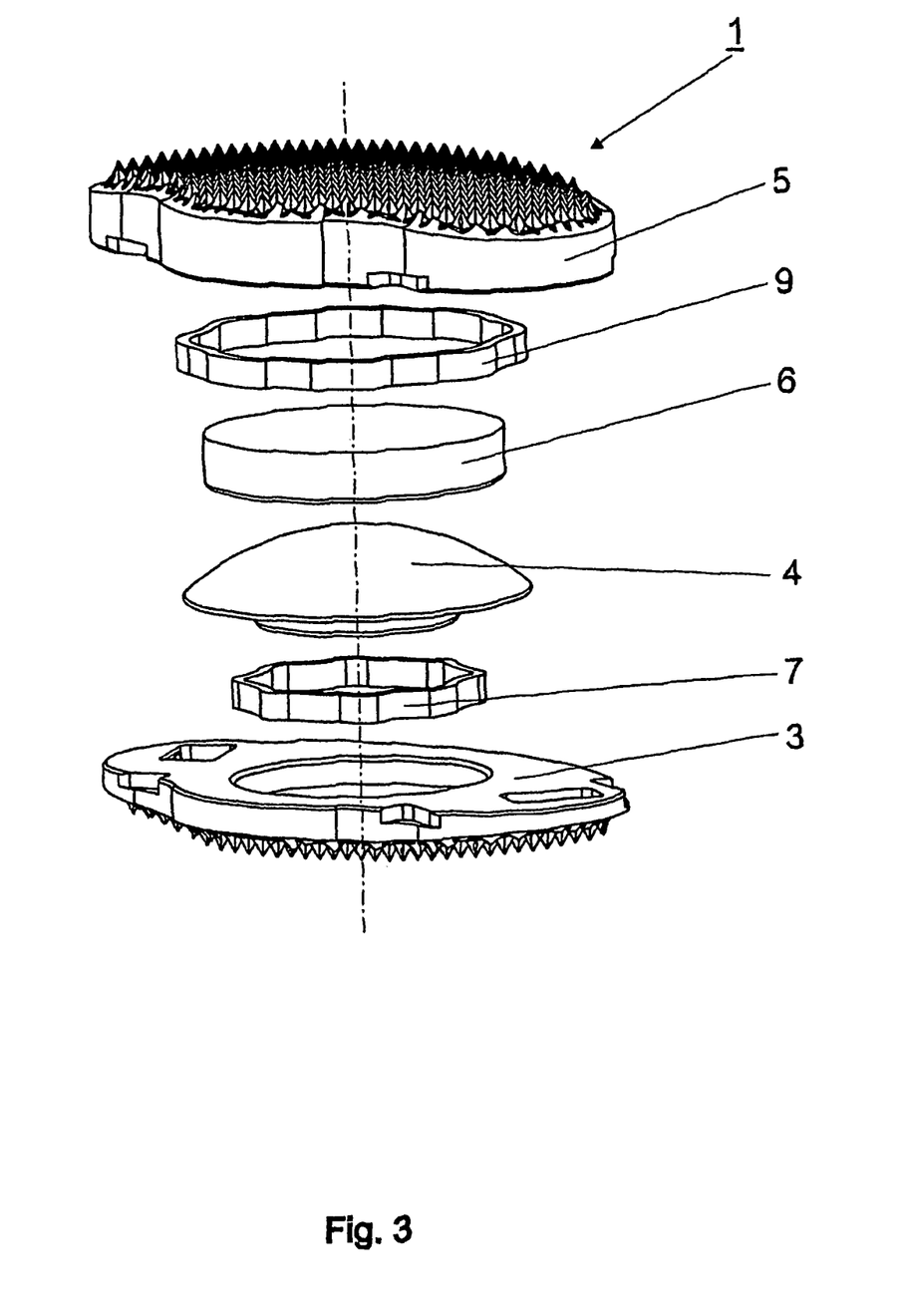
FIG. 3 illustrates an exploded view of another embodiment of the total disc replacement device according to the invention.
Figure 4:
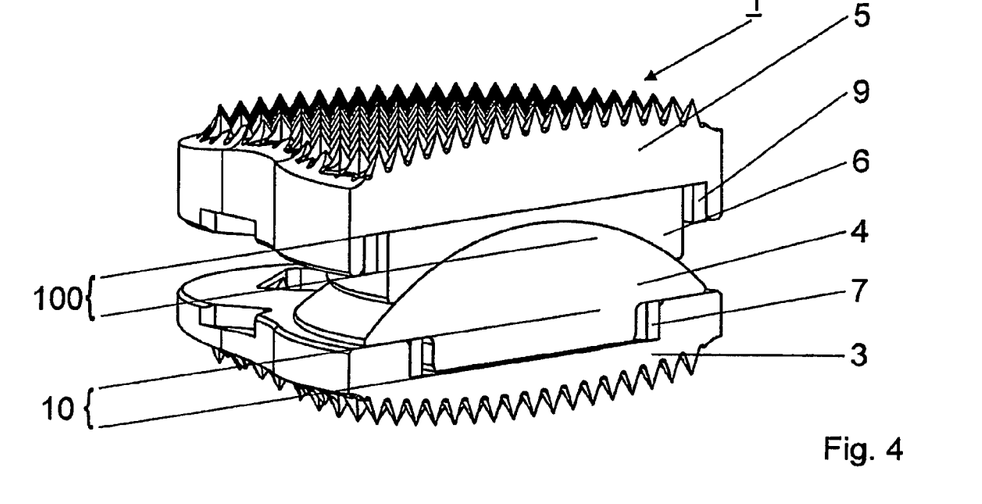
FIG. 4 illustrates a cross-section through the embodiment of FIG. 3.
Figure 5:
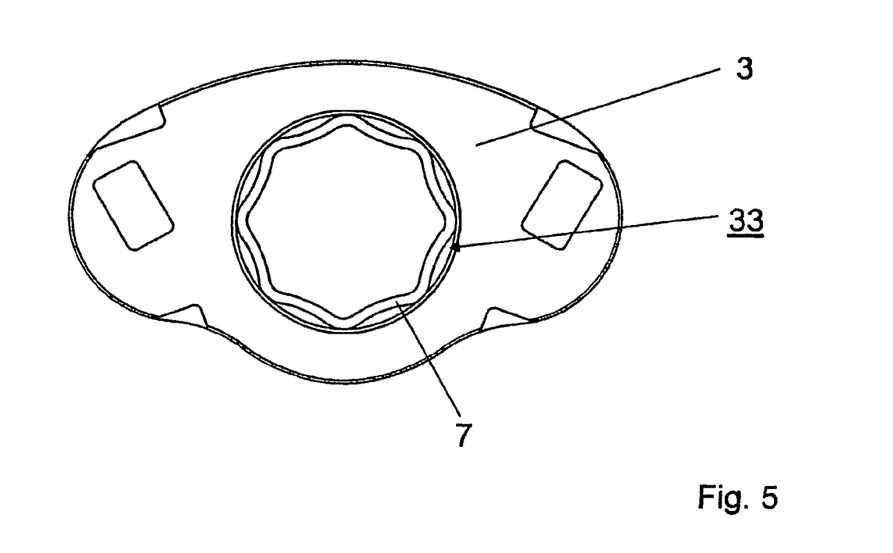
FIG. 5 illustrates a top view on the first apposition member of the device of FIG. 3.

FIGS. 3-5 show a further embodiment of the total disc replacement device 1, whereby the intermediate means 7;9 are designed as a spring-like element. In contrast to the embodiment according to FIGS. 1 and 2 comprising a cylindrically shaped intermediate means 7;9 the embodiment according to FIG. 3 does not require a circular lip forming a positive fit, but allows a frictional fit or connection between the intermediate means 7;9 and the corresponding apposition plates 3;5. FIG. 5 shows the intermediate means 7 being frictionally locked in the first recess 33 of the first apposition plate 3. After the insertion of the cylindrical projections 43 of the first joint component 4 into the first recess 33 of the first apposition plate 3 respectively the second end portion 62 of the second joint component 6 into the second recess 53 of the second end apposition plate 5 the intermediate means 7;9 acting as a spring are plastically or elastically deformed and are clamped over the first and second attachment zones 10;100 with a press fit (FIG. 4).

Figure 6:
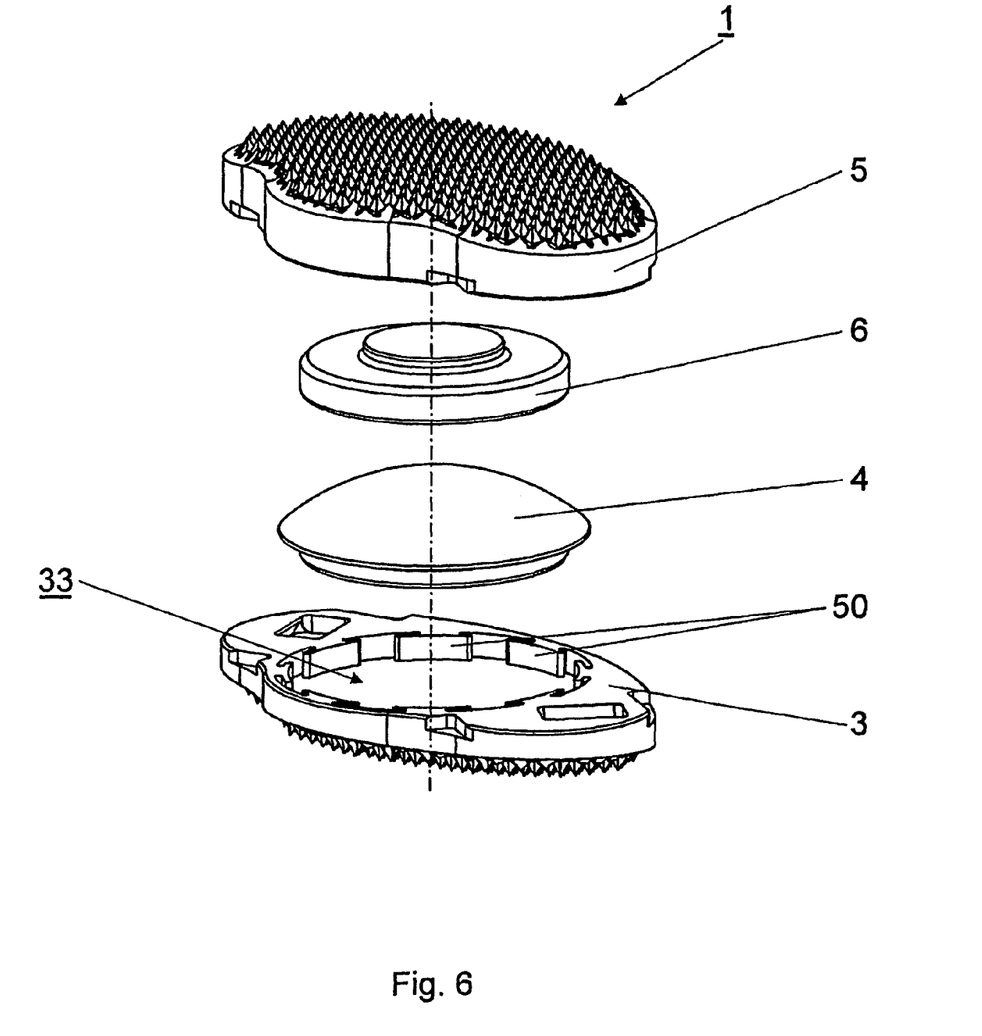
FIG. 6 illustrates an exploded view of a further embodiment of the total disc replacement device according to the invention.

FIG. 6 shows a further embodiment of the total disc replacement device 1, whereby the intermediate means and the corresponding apposition plates consist of one piece and the intermediate means are designed as a plurality of projections 50 formed in a T-shape configuration and being disposed on the periphery of the first and second recess 33;53.

Figure 7:
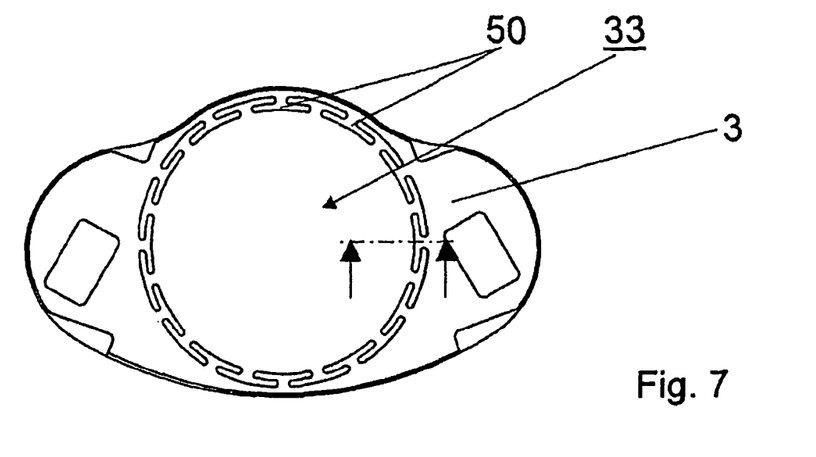
FIG. 7 illustrates a top view on the first apposition member of the device of FIG. 6.

FIG. 7 shows a top view on the first apposition member 3 of the total disc replacement device according to FIG. 6 with the first recess 33 being provided with T-shaped projections 50 on the periphery of said recess 33.

Figure 8:
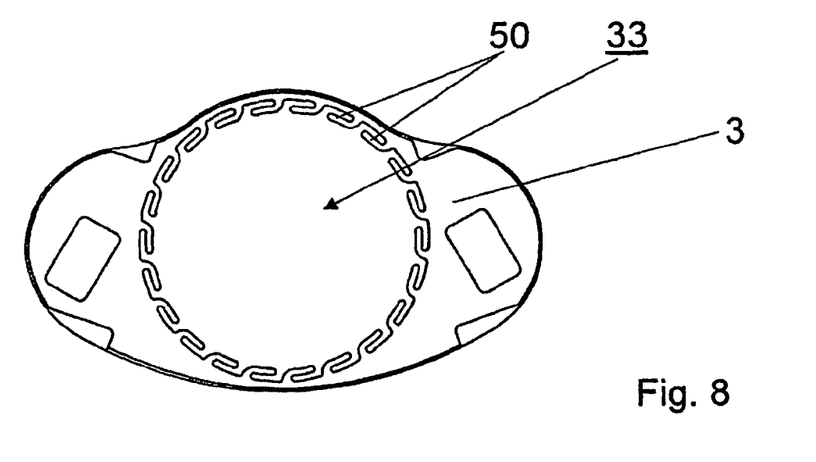
FIG. 8 illustrates a top view on a further embodiment of the first apposition member of the total disc replacement device.

FIG. 8 shows a top view of a further embodiment of the first apposition member of the total disc replacement device with the intermediate means and the first apposition plate 3 consisting of one piece, whereby the intermediate means are preformed as a plurality of L-shaped projections 50.

Figure 9:
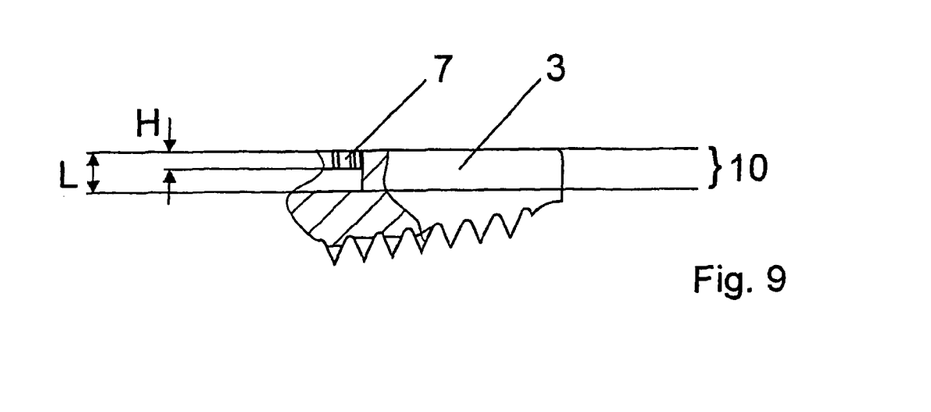
FIG. 9 illustrates a cross-section through the first apposition plate of the total disc replacement device.

FIG. 9 shows a cross-section through the first apposition plate 3 of a further embodiment of the total disc replacement device 1, whereby the height H of the intermediate means 7 is smaller then the height L of the attachment zone 10.

The invention claimed is:

1. An intervertebral implant for implantation between first and second vertebral bodies the intervertebral implant defining a central axis that is extendable into the first and second vertebral bodies when the intervertebral implant is in an intervertebral space, the intervertebral implant comprising:

a first apposition plate having a first contact surface and a first intermediate surface opposite to the first contact surface along the central axis, the first contact surface configured to contact at least a portion of the first vertebral body, the first apposition plate defining a first recess that extends from the first intermediate surface toward the first contact surface along the central axis, and a first inner wall that extends at least along the central axis so as to define the first recess;

a second apposition plate having a second contact surface and a second intermediate surface opposite the second contact surface along the central axis, the second contact surface configured to contact at least a portion of the second vertebral body, the second apposition plate defining a second recess that extends from the second intermediate surface toward the second contact surface along the central axis, the second apposition plate defining a second inner wall that extends at least along the central axis so as to define the second recess;

a first joint component coupled to the first apposition plate, the first joint component including a convex portion and a projection that extends from the convex portion along the central axis, the convex portion defining a convex articulating surface, the projection defining a projection outer surface the convex portion including an outermost periphery and a transverse surface that extends from the projection to the outermost periphery along a transverse direction that is perpendicular to the central axis, wherein at least a portion of the transverse surface is in contact with the first intermediate surface such that the projection protrudes into the first recess;

a second joint component defining a second end that extends into the second recess and is coupled to the second apposition plate, a concave articulating surface opposite to the second end, an outer surface extending between the second end and the concave articulating surface, the concave articulating surface configured to contact the convex articulating surface;

a first ring that couples the first joint component to the first apposition plate, the first ring disposed in the first recess, wherein the first ring defines a first bore that extends through the first ring, the first bore is sized to receive the projection therethrough such that at least a portion of the projection is in contact with a portion of the of the first inner surface of the first apposition plate, wherein the first ring extends from the projection outer surface to the first inner wall along the transverse direction so as to couple the first joint component to the first apposition plate; and a second ring that couples the second joint component to the second apposition plate, the second ring at least partly disposed in the second recess, wherein the second ring extends along the transverse direction from the outer surface of the second joint component to the second inner wall of the second apposition plate so as to couple the second joint component to the second apposition plate.

2. The intervertebral implant of claim 1, wherein the second ring defines a second bore that extends through the second ring, the second end of the second joint component is received in the second bore, wherein at least a portion of the second end is in contact with a portion of the second inner wall of the second apposition plate.

3. The intervertebral implant of claim 1, wherein the projection is a cylindrical projection.

4. The intervertebral implant of claim 1, wherein the projection and the first recess define a first attachment zone and the second end of the second joint component and the second recess define a second attachment zone, the first and second rings being disposed between the first and second apposition plates and the corresponding first and second joint components only within the first and second attachment zones.

5. The intervertebral implant of claim 1, wherein a clearance-free connection is established between 1) the projection and the first inner wall so that no space exists between the first apposition plate and the projection, and 2) between the second end of the second joint component and the second inner wall so that no space exists between the second apposition plate and the second joint component.

6. The intervertebral implant of claim 1, wherein the first and second rings are coupled to the first and second apposition plates, respectively, via a snap-fit connection.

7. The intervertebral implant of claim 6, wherein the first inner wall includes a circular undercut configured to receive a circular lip formed on an outer surface of the first ring.

8. The intervertebral implant of claim 7, wherein the first ring further includes a first flange that extends from the outer surface of the first ring, the first flange being spaced from the lip so as to define a groove that extends between the first flange and the lip, and the first inner wall includes a diametrically enlarged section configured to be received by the groove.

9. The intervertebral implant of claim 7, wherein the second inner wall includes a circular undercut configured to receive a circular lip formed on an outer surface of the second ring.

10. The intervertebral implant of claim 9, wherein the second ring includes a second flange, the second flange extends from the outer surface of the second ring, the second flange spaced from the lip of the second ring so to define a groove, and the second inner wall includes a diametrically enlarged section configured to be received by the groove.

11. The intervertebral implant of claim 1, wherein the first and second apposition plates are coupled to their respective first and second rings via a press-fit connection.

12. The intervertebral implant of claim 1, wherein the first and second rings are one of elastically deformable or plastically deformable.

13. The intervertebral implant of claim 1, wherein the first and second apposition plates are manufactured from a material having a first Young's modulus, the first and second joint components are manufactured from a material having a second Young's modulus and the first and second rings are manufactured from a material having a third Young's modulus, the third Young's modulus being less than the first and second Young's modulus.

14. The intervertebral implant of claim 1, wherein the first and second rings are manufactured from a polymer.

15. The intervertebral implant of claim 1, wherein the first and second joint components are manufactured from a ceramic.

16. The intervertebral implant of claim 1, wherein the first and second apposition plates are manufactured from a metal, the first and second joint components are manufactured from a ceramic and the first and second rings are manufactured from a polymer.

17. The intervertebral implant of claim 1, wherein the first ring defines a ring inner surface and a ring outer surface spaced from the ring inner surface along the transverse direction, wherein 1) the ring inner surface of the first ring abuts at least a portion of the outer surface of the projection, and 2) the ring outer surface of the first ring is coupled directly to the first inner wall.

18. The intervertebral implant of claim 1, wherein the second ring defines a second ring inner surface and a second ring outer surface spaced from the second ring inner surface along the transverse direction, wherein 1) the second ring inner surface abuts at least a portion of the outer surface of the second joint component, and 2) the second ring outer surface is coupled directly to the second inner wall of the second recess.

19. An intervertebral implant configured to be implanted in an intervertebral space between a first and second vertebrae, the intervertebral implant defining a central axis that is extendable into the first and second vertebrae when the intervertebral implant is in the intervertebral space, the intervertebral implant comprising:

a first plate defining a first contact surface configured to contact the first vertebra, a first intermediate surface spaced from the first contact surface along the central axis, and a first recess that extends from the first intermediate surface along the central axis toward the first contact surface, the first plate further defining a first inner wall that extends from the first intermediate surface at least along the central axis toward the first contact surface so as to define the first recess;

a first joint component coupled to the first plate, the first joint component including a convex portion and a projection that extends from the convex portion along the central axis, the convex portion defining a convex articulating surface, the projection defining a projection outer surface, the convex portion including an outermost periphery and a transverse surface that extends from the projection to the outermost periphery along a transverse direction that is perpendicular to the central axis, wherein at least a portion of the transverse surface is in contact with the first intermediate surface such that the projection protrudes into the first recess;

a first ring in the first recess that couples the first joint component to the first plate, the first ring defining a first bore that is sized receive the projection therethrough, wherein the first ring extends from the projection outer surface to the first inner wall along the transverse direction;

a second plate opposed to the first plate along the central axis, the second plate defining a second contact surface, a second intermediate surface opposite the second contact surface, and a second recess that extends from the second intermediate surface toward the second contact surface along the central axis;

a second joint component disposed in the second recess and coupled to the second plate, the second joint component defining an end, a concave articulating surface spaced from the end along the central axis, and an outer surface that extends between the end and the concave articulating surface, wherein the concave articulating surface is in contact with a portion of the convex articulating surface; and a second ring in the second recess that couples the second joint component to the second plate, wherein the second ring extends along the transverse direction from the outer surface of the second joint component to the second inner wall of the second apposition plate.

20. The intervertebral implant of claim 19, wherein the first recess has a first recess cross-sectional dimension and the second recess has a second recess cross-sectional dimension that is less than the first recess cross-sectional dimension.

21. The intervertebral implant of claim 19, wherein the first inner wall includes an undercut configured to receive a lip formed on an outer surface of the first ring.

22. The intervertebral implant of claim 21, wherein the first ring further includes a flange that extends from the outer surface of the first ring, the first flange being spaced from the lip so as to define a groove that extends therebetween, wherein the first inner wall includes an enlarged section that is received by the groove.

23. The intervertebral implant of claim 22, wherein the second inner wall includes a second undercut that receives a second lip formed on an outer surface of the second ring.

24. The intervertebral implant of claim 23, wherein the second ring includes a second flange that extends from the outer surface thereof, the second flange spaced from the second lip of the second ring so to define a second groove extending therebetween, and the second inner wall includes an enlarged section that is received by the second groove.

25. The intervertebral implant of claim 19, wherein the first plate is coupled to the first ring via a press-fit connection.

26. The intervertebral implant of claim 19, wherein first ring has an upper surface that extends along the transverse direction, wherein the transverse surface is in contact with the upper surface of the first ring.

27. The intervertebral implant of claim 19, wherein the first and second rings are one of elastically deformable or plastically deformable.

28. The intervertebral implant of claim 19, wherein at least one of the first and second rings are manufactured from a polymer.

29. The intervertebral implant of claim 19, wherein at least one of the first and second joint components are manufactured from a ceramic.

30. The intervertebral implant of claim 19, wherein at least one of the first and second plates are manufactured from a metal.

31. The intervertebral implant of claim 19, wherein the first and second plates are manufactured from a material having a first Young's modulus, the first and second joint components are manufactured from a material having a second Young's modulus and the first and second rings are manufactured from a material having a third Young's modulus, the third Young's modulus being less than the first and second Young's modulus.

* * * * *

UNITED STATES PATENT AND TRADEMARK OFFICE
CERTIFICATE OF CORRECTION

PATENT NO. : 8,679,181 B2
APPLICATION NO. : 12/438088
DATED : March 25, 2014
INVENTOR(S) : Lechmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1126 days.

Signed and Sealed this
Twenty-ninth Day of September, 2015

Michelle K. Lee
*Director of the United States Patent and Trademark Office*